United States Patent
Tseng et al.

(10) Patent No.: US 9,259,451 B2
(45) Date of Patent: Feb. 16, 2016

(54) USE OF ALCOHOL EXTRACT OF LONGAN SEEDS

(71) Applicant: JOBEN BIO-MEDICAL CO., LTD., Pingtung County (TW)

(72) Inventors: Huang-Chung Tseng, Pingtung County (TW); Yi-Ting Hsiao, Pingtung County (TW); You-Zhong Zhan, Pingtung County (TW); Chun-Yi Yen, Pingtung County (TW); Jian-Sheng Lin, Pingtung County (TW)

(73) Assignee: JOBEN BIO-MEDICAL CO., LTD., Pingtung County (TW)

( * ) Notice: Subject to any disclaimer, the term of this patent is extended or adjusted under 35 U.S.C. 154(b) by 46 days.

(21) Appl. No.: 13/845,614

(22) Filed: Mar. 18, 2013

(65) Prior Publication Data

US 2014/0093597 A1 Apr. 3, 2014

(30) Foreign Application Priority Data

Sep. 28, 2012 (TW) .............................. 101135704 A

(51) Int. Cl.
*A61K 36/77* (2006.01)
*A61K 36/185* (2006.01)

(52) U.S. Cl.
CPC ............. *A61K 36/77* (2013.01); *A61K 2236/00* (2013.01)

(58) Field of Classification Search
CPC ....................... A61K 2300/00; A23V 2002/00
USPC ....................................................... 424/725
See application file for complete search history.

(56) References Cited

U.S. PATENT DOCUMENTS

2012/0177761 A1* 7/2012 Hou et al. ..................... 424/776

FOREIGN PATENT DOCUMENTS

CN 1163309 A * 10/1997
WO 2011003236 A1 1/2011

OTHER PUBLICATIONS

Viable Herbal Solutions (see cited website www.web.archive.org/web/2000113842/htttp://viable-herbal.com/herbology1/herbs42, copyrighted 1996-2000, pp. 1-3).*
Office action issued on Dec. 24, 2013 to the corresponding Taiwan Patent Application No. 101135704.
Search report issued on Jun. 27, 2013 to the corresponding PCT Patent Application No. PCT/CN2012/082275.
Wang Shu-Xia et al. HPLC-ESI-MS Analysis of Phenolic Compounds in Different Solvent Fractions of Ethanol Extract of Longan Seeds and Their Antioxidant Activities, pp. 196-203, 2011, vol. 32, No. 12.
Li Xue-Hua et al., Study on the Anti—Oxidation Efects of Longan Seeds Ethyl Acetate Fraction, pp. 1969-1971, Lishizhen Medicine and Materia Medica Research 2008 vol. 19 No. 8.
Li Xue-Hua et al., Studies on the Chemical Constituents from the Longan Seeds, Aug. 2009, pp. 524-526, vol. 38, No. 4, Acta Med Univ Sci Technol Huazhong.
Feng, Li et al., Progress in Plant Polyphenols and Their Physiological Functions, 2007, pp. 105-107, vol. 19.
Ju, Hai Song, Diseases of metabolic imbalance of free radicals and antioxidants applications.

* cited by examiner

*Primary Examiner* — Chris R Tate
*Assistant Examiner* — Randall Winston
(74) *Attorney, Agent, or Firm* — WPAT, P.C.; Anthony King

(57) ABSTRACT

The present invention provides use of alcohol extract of longan seeds for manufacturing a drug for treating kidney tissue dysfunction. Preferably, an ethyl acetate sub-fraction of the alcohol extract of longan seeds has a better effect in treating kidney tissue dysfunction.

14 Claims, 8 Drawing Sheets

(a)
(b)

(c)

USE OF ALCOHOL EXTRACT OF LONGAN SEEDS

BACKGROUND OF THE INVENTION

1. Field of the Invention

The invention relates to use of an extract of longan seeds; more particularly, in the treatment of kidney tissue dysfunction.

2. Description of the Related Art

Kidneys are located at both sides of the spine at the rear of abdominal cavity in human body, namely, in an included area where the last rib (the twelfth rib) and the spine are jointed. The basic unit of the kidney is nephron, each kidney includes about one million nephrons, and each nephron includes renal glomeruli and renal tubules.

Functions of the nephrons include: filtering wastes, water and electrolytes of the body, and producing urine, for example, removing excessive water; and removing uric acid, urea, creatinine and medicines; and controlling stabilization and balance of electrolytes such as sodium, potassium, calcium, phosphorus, and acids and bases, and maintaining stabilization of the in vivo environment. In addition to mechanism of producing urine, the kidneys can further excrete: (1) erythropoietin, if renal injuries leads to erythropoietin hyposecretion, anemia occurs; (2) D3 for activating vitamins, which is the most important ingredient for maintaining the balance of calcium and phosphorus in blood, so renal failure may lead to bone lesions; and (3) rennin and angiotensin, for adjusting blood pressure, and therefore many types of hypertension are related to kidney troubles.

Many factors are causes of kidney tissue dysfunctions: (1) congenital kidney diseases, such as polycystic kidney disease, and hereditary nephritis and urinary tact abnormalities; (2) glomerulopathy, such as primary glomerulonephritis and secondary glomerulonephritis, for example, diabetes mellitus, hypertension and lupus erythematosus; (3) tubular interstitial nephropathy, such as nephrolithiasis, renal tumor, and urethral or ureteral stricture; (4) vascular kidney diseases, such as vasculitis and hypertension nephrosclerosis; and (5) infection, such as nephritis caused by bacterial infections. In addition, due to aging, long-term drug abuse, family inheritance and high-salt diet, obesity, high cholesterol, smoking and alcohol are causes of kidney tissue dysfunctions. The clinical symptoms include changes in urine pattern such as hyperuresis (especially in night), hematuria, urine blister (urinary protein may be contained); and physical discomfort, such as eyelid edemas or face, hands and feet edema, high blood pressure, anemia, itchy skin, general tiredness, heart failure and pulmonary edema.

However, there are many causes of kidney tissue dysfunctions, there is no effective drugs that can effectively treat kidney tissue dysfunctions, for example, in treatment of secondary kidney tissue dysfunctions, primary focuses are treated to control the disease; in treatment of kidney tissue dysfunctions caused by infections, antibiotics need to be used and in treatment of nephritis, not only common anti-inflammatory agents cannot be used, but also the symptoms get more severe due to use of the common anti-inflammatory agents, and steroids or immunosuppressants are generally used, but serious side effects are serious are caused. Therefore, when the course of kidney tissue dysfunctions is continuously developed, treatment such as peritoneal dialysis even renal transplantation is required, which has great influence on the patient's living and life.

Longan is the fruit of the Family Sapindaceae and Genus *Dimocarpus* plant, and also called as Guiyuan. Longan can be used in herbal medicine. The pulp has a sweet taste and is warm in nature, and has the effect of invigoration; the stone has an astringent taste and is neutral in nature, and has the effect of convergence and stopping bleeding; the leave has a light taste and is neutral in nature, and has the effect of resolving superficies syndrome. Longan has a variety functions such as invigoration and benefiting qi, helping building blood, invigorating heart and spleen, nourishing blood and tranquilizing mind, moisturizing skin and beautification, and can be used to treat anemia, palpitations, insomnia, amnesia, neurasthenia and post-illness and postpartum weakness. Longan seed is used in trauma treatment since ancient times, and as recorded in ancient book A Collection of Chinese Herbal Medicines, longan stone can be used in the treatment of stomach pain, burn and scald wounds, bleeding, ulcer pain, trauma bleeding, scabies and eczema. When being used for trauma treatment by ancients, longan seed has good hemostatic effect, pain-relieving effect and function of regeneration of tissues, and is known as "Jindao Dusheng San". In recent years, studies related to the health care effects of longan, especially studies in the antioxidant capacity, effective ingredients and whitening capability are gradually increasing. Most studies have found that, the flower and fruit of longan have high-level antioxidants, such as gallic acid, corilagin) and ellagic acid. However, studies on longan seed are relatively few. Generally, after longan pulp is obtained, longan seed is abandoned.

Although many uses of longan have been reported, different uses of the extract of longan seeds are still to be developed.

SUMMARY OF THE INVENTION

The present invention provides use of an alcohol extract of longan seeds in the manufacture of a medicament of the treatment of kidney tissue dysfunction.

The invention also provides a method for treating kidney tissue dysfunction in a subject, which comprises administering to said subject an effective amount of an alcohol extract of longan seeds and optionally a pharmaceutically acceptable carrier or excipient.

The invention also provides a pharmaceutical composition for treating kidney tissue dysfunction comprising an alcohol extract of longan seeds and optionally a pharmaceutically acceptable carrier or excipient.

The invention still also provides a process for preparing an alcohol extract of longan seeds comprising:
(a) providing longan seeds;
(b) cutting the longan seeds into small pieces; and
(c) extracting the small pieces in step (b) with the alcohol to obtain an extract.

DETAILED DESCRIPTION OF THE INVENTION

Figure 1:
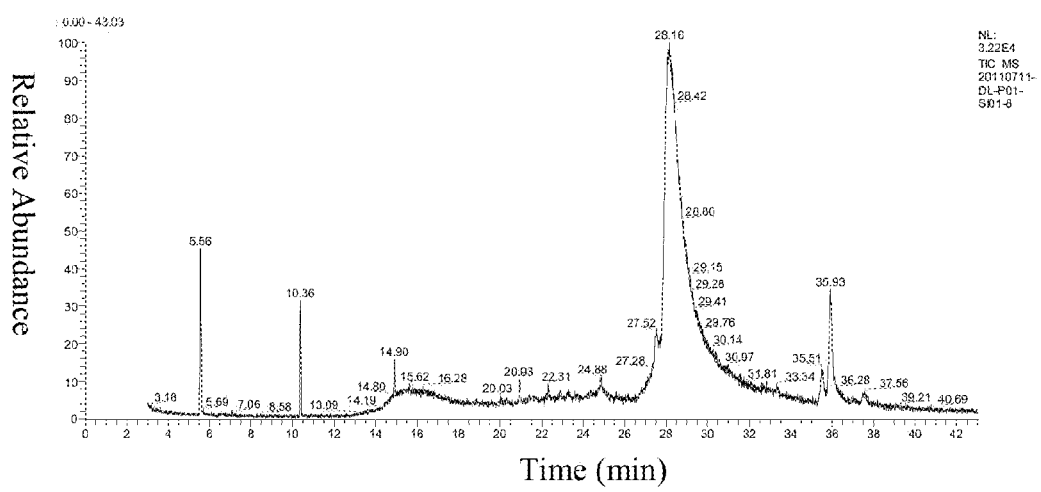
FIG. 1 illustrates the GC-MS spectrogram of the alcohol extract of longan seeds according to the invention.

The present invention provides use of an alcohol extract of longan seeds in the manufacture of a medicament of the treatment of kidney tissue dysfunction. The pharmaceutical composition comprising the alcohol extract of longan seeds is used for treating kidney tissue dysfunction, and the pharmaceutical composition comprises an alcohol extract of longan seeds and optionally a pharmaceutically acceptable carrier or excipient.

The present invention can be more readily understood by reference to the following detailed description of various embodiments of the invention, the examples, and the chemical drawings and tables with their relevant descriptions. It is to be understood that unless otherwise specifically indicated by the claims, the invention is not limited to specific preparation methods, carriers or formulations, or to particular modes of formulating the extracts of the invention into products or compositions intended for topical, oral or parenteral administration, because as one of ordinary skill in the relevant arts is well aware, such things can, of course, vary. It is also to be understood that the terminology used herein is for the purpose of describing particular embodiments only and is not intended to be limiting.

As utilized in accordance with the present disclosure, the following terms, unless otherwise indicated, shall be understood to have the following meaning:

Often, ranges are expressed herein as from "about" one particular value and/or to "about" another particular value. When such a range is expressed, an embodiment includes the range from the one particular value and/or to the other particular value. Similarly, when values are expressed as approximations, by use of the word "about," it will be understood that the particular value forms another embodiment. It will be further understood that the endpoints of each of the ranges are significant both in relation to and independently of the other endpoint. As used herein the term "about" refers to ±10%.

"Optional" or "optionally" means that the subsequently described event or circumstance may or may not occur, and that the description includes instances where said event or circumstance occurs and instances where it does not. For example, the phrase "optionally comprising an agent" means that the agent may or may not exist.

It must be noted that, as used in the specification and the appended claims, the singular forms "a," "an" and "the" include plural referents unless the context clearly dictates otherwise. Thus, unless otherwise required by context, singular terms shall include the plural and plural terms shall include the singular.

The term "subject" as used herein denotes any animal, preferably a mammal, and more preferably a human. The examples of subjects include humans, non-human primates, rodents, guinea pigs, rabbits, sheep, pigs, goats, cows, horses, dogs and cats.

The term "effective amount" of an active ingredient as provided herein means a sufficient amount of the ingredient to provide the desired regulation of a desired function, such as gene expression, protein function, or the induction of a particular type of response. As will be pointed out below, the exact amount required will vary from subject to subject, depending on the disease state, physical conditions, age, sex, species and weight of the subject, the specific identity and formulation of the composition, etc. Dosage regimens may be adjusted to induce the optimum therapeutic response. For example, several divided doses may be administered daily or the dose may be proportionally reduced as indicated by the exigencies of the therapeutic situation. Thus, it is not possible to specify an exact "effective amount." However, an appropriate effective amount can be determined by one of ordinary skill in the art using only routine experimentation.

The term "treating" or "treatment" as used herein denotes reversing, alleviating, inhibiting the progress of or improving the disorder or condition to which such term applies, or one or more symptoms of such disorder or condition.

The term "carrier" or "excipient" as used herein refers to any substance, not itself a therapeutic agent, used as a carrier and/or diluent and/or adjuvant, or vehicle for delivery of a therapeutic agent to a subject or added to a formulation to improve its handling or storage properties or to permit or facilitate formation of a dose unit of the composition into a discrete article such as a capsule or tablet suitable for oral administration. Suitable carriers or excipients are well known to persons of ordinary skill in the art of manufacturing pharmaceutical formulations or food products. Carriers or excipients can include, by way of illustration and not limitation, buffers, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable carriers or excipients include citrate buffer, phosphate buffer, acetate buffer, bicarbonate buffer, stearic acid, magnesium stearate, magnesium oxide, sodium and calcium salts of phosphoric and sulfuric acids, magnesium carbonate, talc, gelatin, acacia gum, sodium alginate, pectin, dextrin, mannitol, sorbitol, lactose, sucrose, starches, gelatin, cellulosic materials (such as cellulose esters of alkanoic acids and cellulose alkyl esters), low melting wax cocoa butter, amino acids, urea, alcohols, ascorbic acid, phospholipids, proteins (for example, serum albumin), ethylenediamine tetraacetic acid (EDTA), dimethyl sulfoxide (DMSO), sodium chloride or other salts, liposomes, mannitol, sorbitol, glycerol or powder, polymers (such as polyvinyl-pyrrolidone, polyvinyl alcohol, and polyethylene glycols), and other pharmaceutically acceptable materials. The carrier should not destroy the pharmacological activity of the therapeutic agent and should be non-toxic when administered in doses sufficient to deliver a therapeutic amount of the agent.

Preferably, the alcohol extract of longan seeds is comprised in a composition. The composition of the invention is preferably a food composition or a pharmaceutical composition.

The alcohol extract of longan seeds can be added to a conventional food composition (i.e. the edible food or drink or precursors thereof) in the manufacturing process of the food composition. Almost all food compositions can be supplemented with the alcohol extract of longan seeds of the invention. The food compositions that can be supplemented with the alcohol extract of longan seeds of the invention include, but are not limited to, candies, baked goods, ice creams, dairy products, sweet and flavor snacks, snack bars, meal replacement products, fast foods, soups, pastas, noodles, canned foods, frozen foods, dried foods, refrigerated foods, oils and fats, baby foods, or soft foods painted on breads, or mixtures thereof.

The pharmaceutical composition of the invention is preferably administered topically or systemically by any method known in the art, including, but not limited to, intramuscular, intradermal, intravenous, subcutaneous, intraperitoneal, intranasal, oral, mucosal or external routes. The appropriate route, formulation and administration schedule can be determined by those skilled in the art. In the present invention, the pharmaceutical composition can be formulated in various ways, according to the corresponding route of administration, such as a liquid solution, a suspension, an emulsion, a syrup, a tablet, a pill, a capsule, a sustained release formulation, a powder, a granule, an ampoule, an injection, an infusion, a kit, an ointment, a lotion, a liniment, a cream or a combination thereof. If necessary, it may be sterilized or mixed with any pharmaceutically acceptable carrier or excipient, many of which are known to one of ordinary skill in the art.

As used herein, the term "alcohol extract of longan seeds" refers to an extract obtained by extracting longan seeds with an alcohol solution. The manner of extracting seeds with a solution is well-known to artisans skilled in this field. In one preferred embodiment of the invention, the longan seeds are soaked in the alcohol solution for extraction; more preferably, the longan seeds are soaked in the alcohol solution and subjected to ultrasonic vibration extraction.

In one preferred embodiment of the invention, the alcohol extract of longan seeds is subjected to a Gas Chromatography-Mass Spectrophotometry (GC-MS) assay. The gas chromatography is conducted with Trace GC Ultra, thermo; and the mass spectrophotometry is conducted with ITQ 900, thermo; the column is Varian® VF-5 ms 30 m×0.25 mm (I.D. 0.25 μm). The temperature program is 150° C. for 5 min; heating to 190° C. at a rate of 5° C./min for 20 min. As shown in FIG. 1, the spectrogram obtained comprises peaks at retention time of about 5.56 min, about 10.36 min, 14.90 min, about 27.52 min, about 28.16 min, about 35.51 min, about 35.93 min, and about 37.56 min.

The longan seeds referred to in this invention are not particularly limited. Preferably, the longan belongs to Sapindaceae family and *Dimocarpus* genus, and also called as Guiyuan. More preferably, the longan is *Dimocarpus longan* Lour., *Dimocarpus longan* or *Dimocarpus longan* Fen Ke.

The longan seed is the nutlet part of longan fruit, and substantially does not include the shell and pulp part. The manner for obtaining the longan seed from the longan fruit is well-known to artisans skilled in this field.

In one preferred embodiment of the invention, the alcohol is selected from the group consisting of methanol, ethanol, n-propanol, isopropanol, n-butanol, iso-butanol, sec-butanol, tert-butanol, and ethyl acetate. More preferably, the alcohol is ethanol, n-butanol or ethyl acetate; most preferably, the alcohol is ethanol. The alcohol solution preferably about 20% to about 99.9% alcohol.

In one preferred embodiment of the invention, the alcohol extract of longan seeds is an ethanol extract of longan seeds.

In one preferred embodiment of the invention, the alcohol extract of longan seeds comprises an ethyl acetate fraction of the alcohol extract of longan seeds.

In another preferred embodiment of the invention, the alcohol extract of longan seeds comprises a water fraction obtained by extracting the alcohol extract of longan seeds with ethyl acetate.

In still another preferred embodiment of the invention, the alcohol extract of longan seeds comprises an n-butanol sub-fraction of the water fraction obtained by extracting the alcohol extract of longan seeds with ethyl acetate.

In still another preferred embodiment of the invention, the alcohol extract of longan seeds comprises a water sub-fraction obtained by extracting the water fraction (obtained by extracting the alcohol extract of longan seeds with ethyl acetate) with n-butanol.

In one more preferred embodiment of the invention, the alcohol extract of longan seeds comprises a fraction obtained by flash column chromatography; the column is 40 g Silica; the flow rate is 18 mL/min; the mobile phase uses Solution A of ethyl acetate and Solution B of methanol; the gradient elution program is 100% Solution A and 0% Solution B at about 0 minute to about 30 minutes; 80% Solution A and 20% Solution B at about 31 minutes to about 45 minutes; 50% Solution A and 50% Solution B at about 46 minutes to about 65 minutes; 0% Solution A and 100% Solution B at about 66 minutes to about 85 minutes and at about 86 minutes to about 100 minutes. Still more preferably, the alcohol extract of longan seeds comprises a fraction obtained by flash column chromatography with the gradient elution program of 100% Solution A and 0% Solution B at about 0 minute to about 30 minutes.

Figure 2:
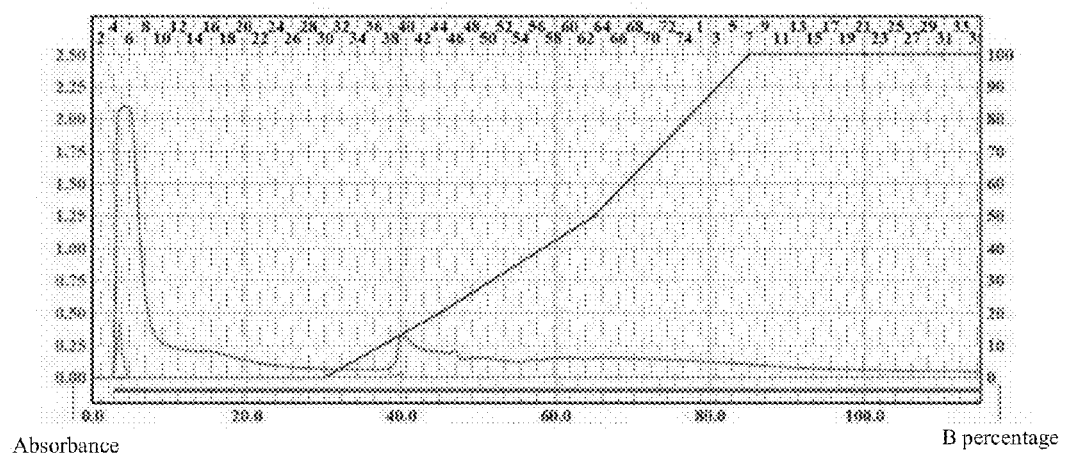
FIG. 2 illustrates the flash chromatography spectrogram of the alcohol extract of longan seeds according to the invention.

In one embodiment of the invention, the results of the ethyl acetate fraction of the alcohol extract of longan seeds isolated by flash column chromatography are shown in FIG. 2, and wherein DL-P01-SI01: 765.3 mg; DL-P01-SI02: 100.4 mg; DL-P01-SI03: 37.0 mg; DL-P01-SI04: 21.7 mg; DL-P01-SI05: 140.1 mg; DL-P01-SI06: 57.3 mg; DL-P01-SI07: 28.4 mg; DL-P01-SI08: 17.0 mg; DL-P01-SI09: 6.4 mg; DL-P01-SI10: 7.7 mg.

The invention still also provides a process for preparing an alcohol extract of longan seeds comprising:
 (a) providing longan seeds;
 (b) cutting the longan seeds into small pieces; and
 (c) extracting the small pieces in step (b) with the alcohol to obtain an extract.

According to the process of the invention, prior to step (b), the longan seeds are preferably dried.

In one preferred embodiment of the invention, step (b) further comprises blending the small pieces into powder. The manner of cutting and/or blending is well-known to artisans skilled in this field.

The ratio (w/v) of the longan seeds and the alcohol solution is not specifically restricted, and can be about 1:1 to about 1:10; preferably about 1:3 to about 1:8; and most preferably about 1:5.

In one preferred embodiment of the invention, the extracting the small pieces in step (b) with the alcohol is with heat. Preferably, the temperature for the extracting in step (c) is about 30° C. to about 90° C.

In one preferred embodiment of the invention, step (c) further comprises:
 (c1) extracting the small pieces in step (b) with an ethanol solution to obtain a rude extract;
 (c2) lyophilizing the rude extract in step (c1); and
 (c3) extracting a product of lyophilizing in step (c2) with ethyl acetate to obtain an ethyl acetate fraction and a water fraction.

Preferably, the rude extract is filtered and condensed prior to lyophilization.

In one more preferred embodiment of the invention, step (c) further comprises (c4) extracting the water fraction with n-butanol to obtain an n-butanol sub-fraction and a water sub-fraction.

In one preferred embodiment of the invention, the preparations of the ethyl acetate fraction, water fraction, n-butanol sub-fraction or water sub-fraction of the alcohol extract of longan seeds are for further extracting the alcohol extract of longan seeds.

In one preferred embodiment of the invention, the process further comprises extracting the ethyl acetate fraction by flash column chromatography; wherein the column is 40 g Silica; the flow rate is 18 mL/min; the mobile phase uses Solution A of ethyl acetate and Solution B of methanol; the gradient elution program is 100% Solution A and 0% Solution B at about 0 minute to about 30 minutes; 80% Solution A and 20% Solution B at about 31 minutes to about 45 minutes; 50% Solution A and 50% Solution B at about 46 minutes to about 65 minutes; 0% Solution A and 100% Solution B at about 66 minutes to about 85 minutes and at about 86 minutes to about 100 minutes.

Preferably, the process further comprises (d) obtaining a liquid fraction from the extract, and a solid fraction is removed. The manner of removing the solid fraction to obtain the liquid fraction is well-known to artisans skilled in this field.

The kidney tissue dysfunction according to the present invention refers to a kidney tissue dysfunction caused by any causes, and preferably, the kidney tissue dysfunction is kidney tissue dysfunction caused by renal tissue necrosis, hypertension, immune injury, diabetes mellitus, systemic lupus erythematosus, aging, long-term drug abuse, family inheritance, high-salt diet, obesity, high cholesterol, smoking, alcohol or nephrectomy.

Detection of whether the kidney tissue function is normal can be diagnosed through the following tests: (1) detection of blood urea nitrogen (BUN) and serum creatinine (Cr) in blood, because kidney tissue dysfunctions cause increase of the two values; (2) detection of index of urinary protein in urine and blood urine, to calculate the glomerular filtration rate, so as to know the kidney function; (3) X-ray examination: the kidney appearance is inspected by X-ray examination, and at the same time, whether a kidney stone exists and the relative position of the kidney stone are detected; and (4) ultrasonic inspection: to know the size of the kidney, whether a kidney stone and tumor exist.

In one embodiment of the present invention, the kidney tissue dysfunction refers to that it is proved by diagnosis and inspection that abnormity is found in the kidney structure (histophysiological or imaging examination) or the kidney function (blood or urine inspection) or the glomerular filtration rate (GFR) is less than 60 cc/min/1.73 $m^2$.

In an animal model of an embodiment of the present invention, in rats with 5/6 kidney resected, administration of the alcohol extract of longan seeds of the present invention can reduce the blood and/or urine urinary protein, reduce the blood urea nitrogen, reduce the urine protein-creatinine ratio, reduce the blood and/or urine creatine kinase, reduce the blood and/or urine lactate dehydrogenase, reduce the blood and/or urine lactic acid and alleviate segmental sclerosis In a preferred specific embodiment of the present invention, the kidney tissue dysfunction is selected from the group consisting of excessively high blood and/or urine urinary protein, excessively high blood urea nitrogen, excessively high urine protein-creatinine ratio, excessively high blood and/or urine creatine kinase, excessively high blood and/or urine lactate dehydrogenase, excessively high blood and/or urine lactic acid and segmental sclerosis.

The following examples are given for the purpose of illustration only and are not intended to limit the scope of the present invention.

EXAMPLE

Alcohol Extract of Longan Seeds

After shelling and removing the pulp from longan fruits, the longan seeds are obtained, and then longan seeds are smashed, and the smashed longan seeds are immersed in a 20% to 95% ethanol solution at a temperature of 30° C. to 90° C., and the temperature is maintained at 30° C. to 90° C. for 1 to 3 hrs. The solution obtained through extraction is filtered, concentrated, and then subjected to low-temperature and low-pressure lyophilized, to obtain a rude extract (DL).

Figure 3:
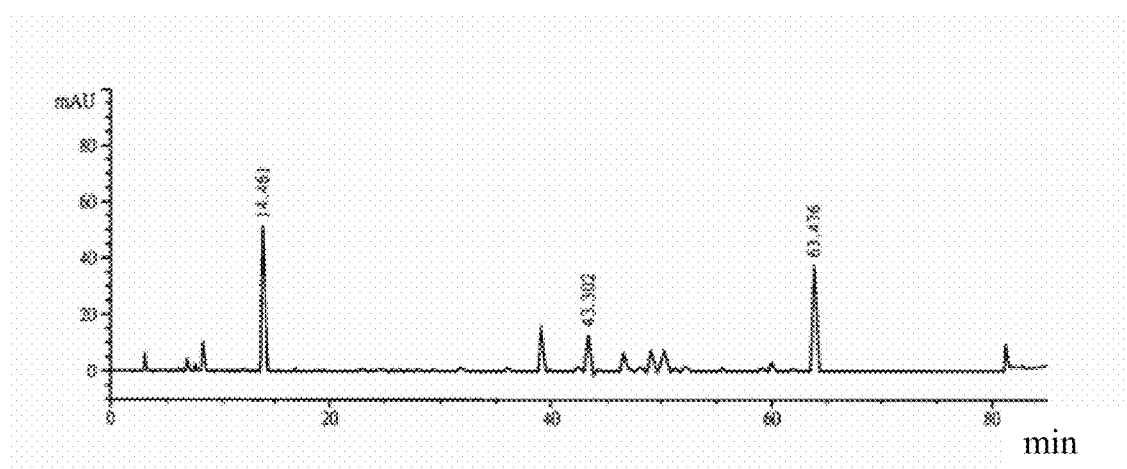
FIG. 3 illustrates the HPLC spectrogram of the alcohol extract of longan seeds according to the invention.

The rude extract is subjected to a high performance liquid chromatography assay as described in Table 1, and the result is shown in FIG. 3.

TABLE 1

| Apparatus | Agilent 1100 | | | | | | |
|---|---|---|---|---|---|---|---|
| Chromatography column | Atlantis ®T35 μm 4.6 × 10 mm, Waters | | | | | | |
| Precolumn | Cosmosil 5C18-AR-II 4.6 × 10 mm, Nacalai Tesque | | | | | | |
| Column temperature | 25° C. | | | | | | |
| Flow rate | 1.0 mL/min | | | | | | |
| Detection wave length | UV 270 nm | | | | | | |
| Injection volumn | 10 μL | | | | | | |
| Time (min) | 0 | 5 | 15 | 30 | 45 | 60 | 75 | 85 |
| 0.1% H3PO4 (%) | 98 | 97 | 97 | 87 | 86 | 81 | 79 | 0 |
| acetonitrile (%) | 2 | 3 | 3 | 13 | 14 | 19 | 21 | 100 |

The rude extract (DL) is further extracted with ethyl acetate to obtain an ethyl acetate fraction (DL-P01) and a water fraction. The water fraction is further extracted with n-butanol to obtain an n-butanol sub-fraction (DL-P02) and a water sub-fraction (DL-P03). After extracting 24.13 g of the rude extract, DL-P01: 1.44 g (5.97%); DL-P02: 2.57 g (10.65%); DL-P03: 19.11 g (79.20%) are obtained.

The ethyl acetate fraction (DL-P01) is further subjected to the flash chromatography. About 1.1 g of DL-P01 is dissolved in ethyl acetate and methanol with the assistance of an ultrasonic cleaner, and then silica gel is added. After condensing to dry, the sample is placed into a empty sample tube. On the other hand, the normal phase column, 40 g silica gel, for the flash chromatography is equipped to the apparatus. The column is saturated with the solvent and the sample is loaded. The program is listed below: the flow rate is 18 mL/min; the mobile phase uses Solution A of ethyl acetate and Solution B of methanol; the gradient elution program is 100% Solution A and 0% Solution B at about 0 minute to about 30 minutes; 80% Solution A and 20% Solution B at about 31 minutes to about 45 minutes; 50% Solution A and 50% Solution B at about 46 minutes to about 65 minutes; 0% Solution A and 100% Solution B at about 66 minutes to about 85 minutes and at about 86 minutes to about 100 minutes.

The results are shown in FIG. 2, and DL-P01-SI01: 765.3 mg; DL-P01-SI02: 100.4 mg; DL-P01-SI03: 37.0 mg; DL-P01-SI04: 21.7 mg; DL-P01-SI05: 140.1 mg; DL-P01-SI06: 57.3 mg; DL-P01-SI07: 28.4 mg; DL-P01-SI08: 17.0 mg; DL-P01-SI09: 6.4 mg; DL-P01-SI10: 7.7 mg are obtained. DL-P01-SI01 is the main product (69.86%) which is collected by flash column chromatography with the gradient elution program of 100% Solution A and 0% Solution B at about 0 minute to about 30 minutes.

About 0.6 mL of methanol is added in 6 mg of the above mentioned DL-P01-SI01 and further subjected to vibration, dissolve, and filtration, and then subjected to a Gas Chromatography-Mass Spectrophotometry (GC-MS) assay. The gas chromatography is conducted with Trace GC Ultra, thermo; and the mass spectrophotometry is conducted with ITQ 900, thermo; the column is Varian® VF-5 ms 30 m×0.25 mm (I.D. 0.25 μm). The temperature program is 150° C. for 5 min; heating to 190° C. at a rate of 5° C./min for 20 min. As shown in FIG. 1, the spectrogram obtained comprises peaks at retention time of about 5.56 min, about 10.36 min, 14.90 min, about 27.52 min, about 28.16 min, about 35.51 min, about 35.93 min, and about 37.56 min.

Alcohol Extract of Longan Seeds in Treatment of Kidney Tissue Dysfunction

In this example, a 5/6 nephrectomized rat model is used to perform in vivo pharmacological activity test and efficacy evaluation of kidney tissue dysfunction.

Sprague-Dawley white rates were adopted, the right kidney and 2/3 left kidney were resected through operation, and one week later, urinary protein in urine was detected to confirm the nephritis syndrome, and then the rats were grouped and subjected to administration tests. The nephritis animal were randomly grouped, including: a pseudo operation group (pseudo operation animal+solvent for formulating agent), a control group (nephritis animal+solvent for formulating agent), an experimental group (nephritis animal+DL-P01-SI01, referred to as J-TK for short), and the number of rats in each group was not less than three. Before administration, continuous observation was performed for eight weeks after drug treatment, blood was sampled at caudal vein and urine sample was collected by a metabolic cage once per week for tracking survey of physiological index data and biochemical analysis of urine and blood, urine was collected before sacrifice at the ninth week, and blood and tissue were collected after sacrifice for biochemical analysis.

The main items for physiological, biochemical analysis include: concentration detection of urinary protein, blood usea nitrogen, creatinine, creatine kinase, lactate dehydrogenase, lactic acid, and blood count measurement.

Figure 4:
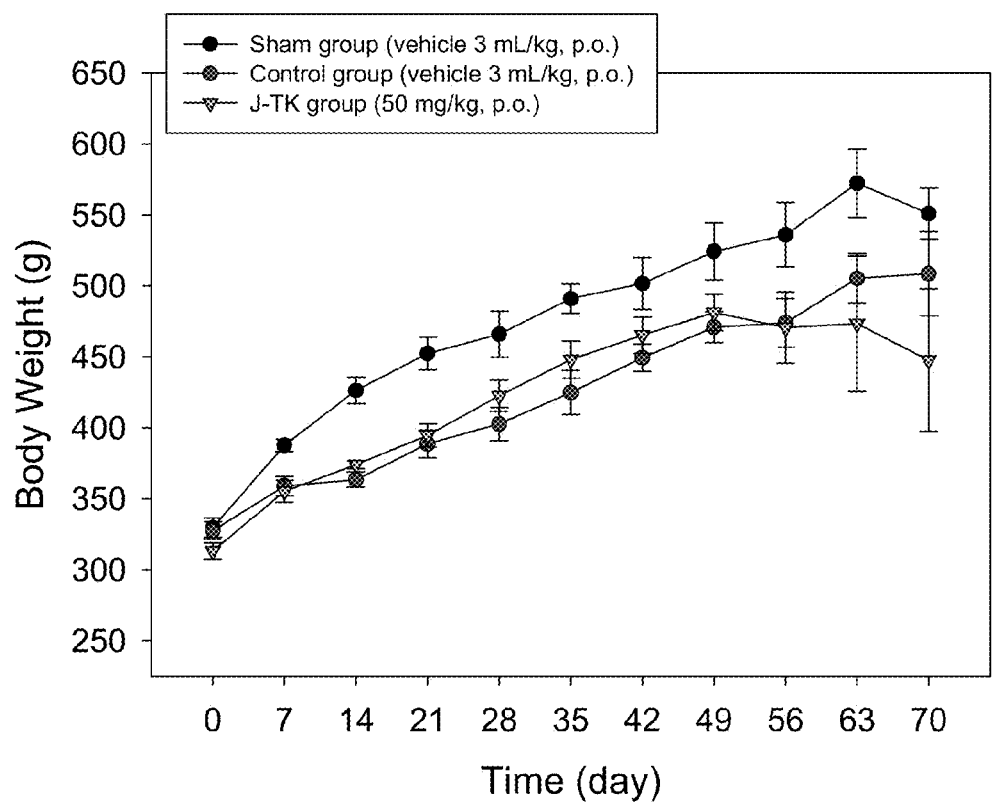
FIG. 4 illustrates the weight-time diagram of the experimental animals in the 5/6 nephrectomized rat model. The solvent for the extract includes 5% DMSO and 10% chlorophyll. The composition is given orally. The data are expressed as mean (n=3 per group).

In this animal model experiment, it can be observed that the weights of the experimental animals are normally is slowly increased, as shown in FIG. 4.

Figure 5:
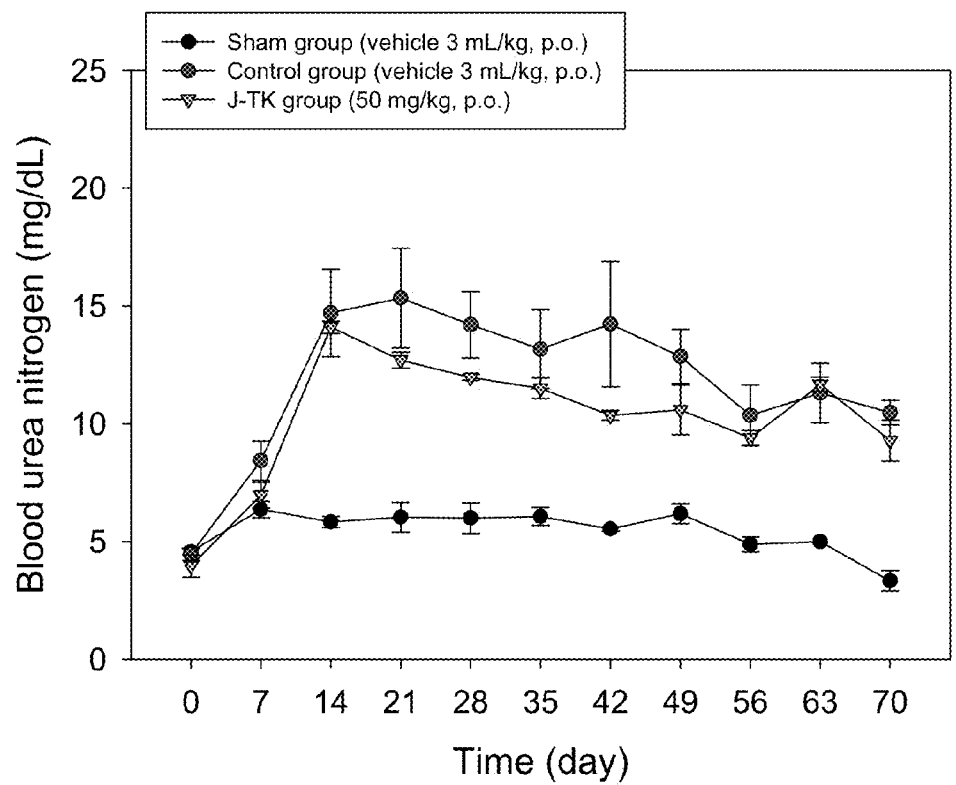
FIG. 5 illustrates the blood urea nitrogen in serum-time diagram of the experimental animals in the 5/6 nephrectomized rat model. The solvent for the extract includes 5% DMSO and 10% chlorophyll. The data are expressed as mean (n=3 per group).
Figure 6:
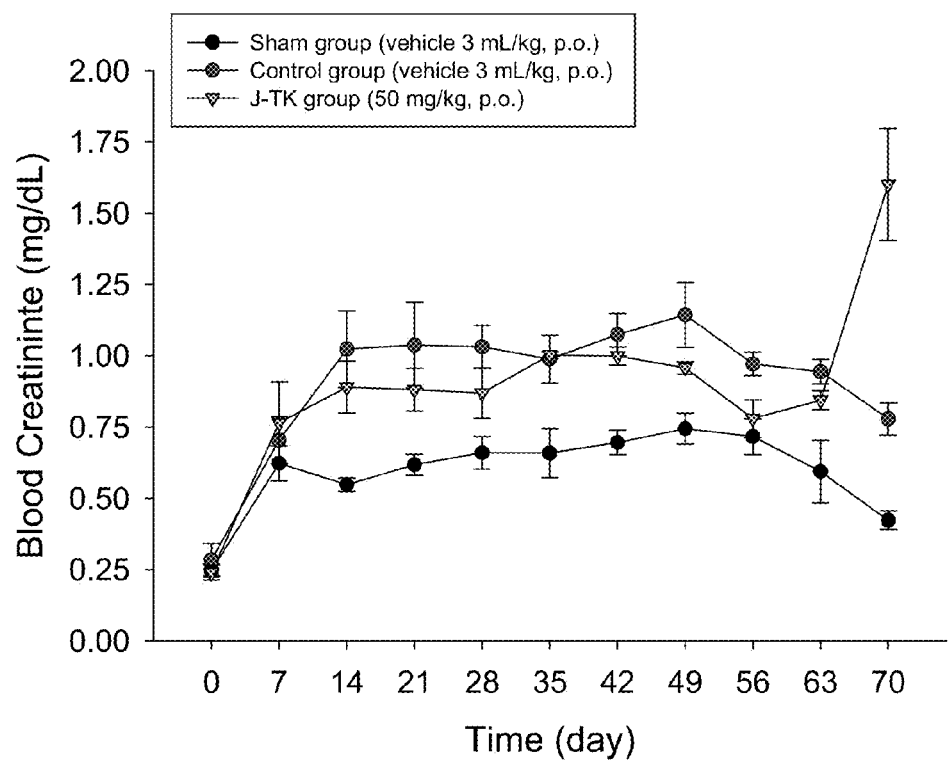
FIG. 6 illustrates the blood creatinine-time diagram of the experimental animals in the 5/6 nephrectomized rat model. The data are expressed as mean (n=3 per group).

Biochemical indexes such as blood usea nitrogen, lactate dehydrogenase, lactic acid, creatinine in serum are detected. After the second operation, it can be found that blood usea nitrogen and creatinine in serum of operation animal are significantly increased. After administration and treatment, it is observed after one-week administration that DL-P01-SI01 (J-TK) can significantly decelerate the increase of blood usea nitrogen and creatinine in serum, and after four-week administration, the inhibition rate of J-TK on blood usea nitrogen in blood is up to 27.2%. The result indicates that in the animal model, the regulation effect on blood usea nitrogen is significant, as shown in FIG. 5 and FIG. 6.

It can be observed from the variation of lactic acid and lactate dehydrogenase that in this experiment, the physiology condition of the animal is not influenced by unexpected diseases, which is not shown in the figures.

Figure 7:
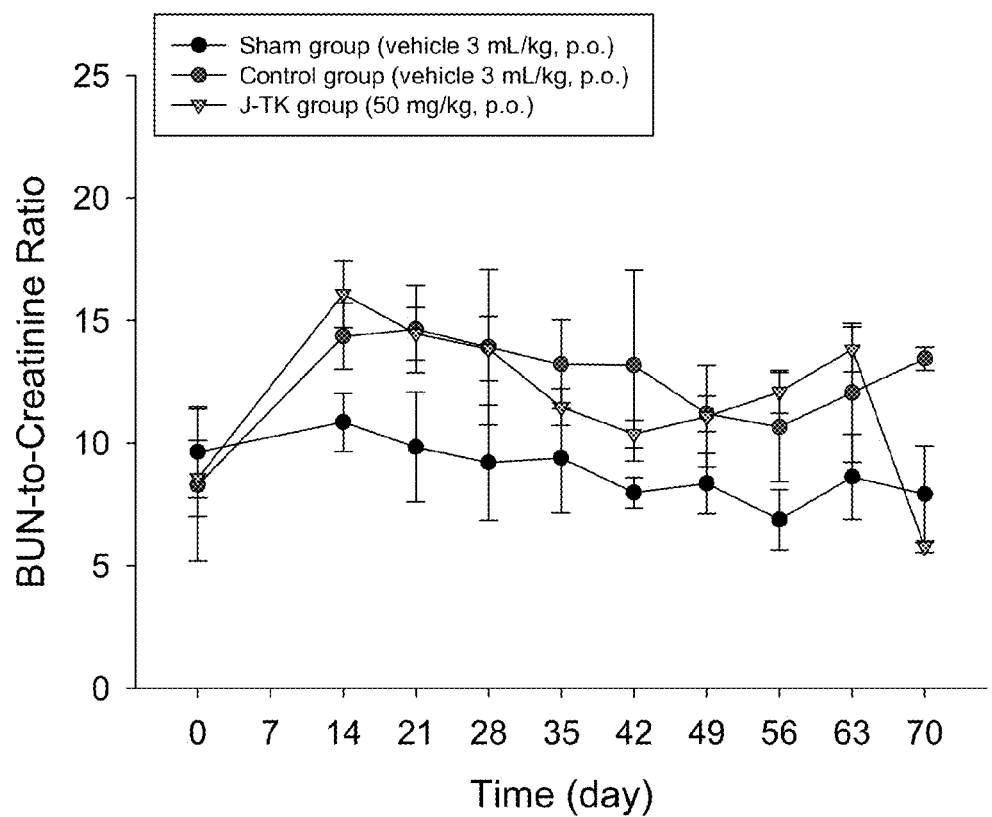
FIG. 7 illustrates the urine protein-creatinine ratio-time diagram of the experimental animals in the 5/6 nephrectomized rat model. The data are expressed as mean (n=3 per group).

The analysis data of urine urinary protein and creatinine are presented by a ratio of single spot urinary protein concentration to urine creatinine concentration, and the results indicates that after nephrectomy, the urinary protein concentration/urine creatinine concentration in animal urine is significantly increased, compared with that of the pseudo operation group, and after three-week administration, the effect of decelerating the increase of the urinary protein concentration/urine creatinine concentration ratio is exhibited, as shown in FIG. 7.

Figure 8:
FIG. 8 illustrates the kidney tissue pathological slices of the experimental animals in the 5/6 nephrectomized rat model.
Figure 8:
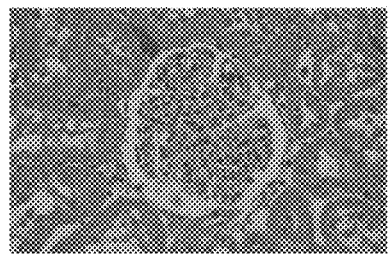
Figure 8:
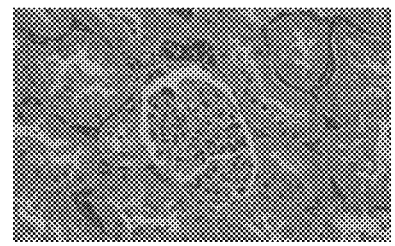

After staining the kidney slice of the experimental animal with H&E, it can be observed that the swelling and sclerosis of glomerulus of animal with 5/6 kidney resected is extremely serious; and after treatment with DL-P01-SI01 (J-TK), the situation is significantly improved, as shown in FIG. 8.

It can be known from the animal model obtained by 5/6 renal resection operation that, the alcohol extract of longan seeds exactly has the effects of decreasing excessively high blood and/or urine urinary protein, excessively high blood urea nitrogen, excessively high urine protein-creatinine ratio, excessively high blood and/or urine creatine kinase, excessively high blood and/or urine lactate dehydrogenase, excessively high blood and/or urine lactic acid and alleviating segmental sclerosis.

While embodiments of the present invention have been illustrated and described, various modifications and improvements can be made by persons skilled in the art. It is intended that the present invention is not limited to the particular forms as illustrated, and that all the modifications not departing from the spirit and scope of the present invention are within the scope as defined in the following claims.

What is claimed is:

1. A method for treating kidney tissue dysfunction to a subject in need thereof, which comprises administering to said subject an effective amount of an alcohol extract of longan seeds and optionally a pharmaceutically acceptable carrier or excipient.

2. The method according to claim 1, wherein the longan is *Dimocarpus longan* Lour., *Dimocarpus longan* or *Dimocarpus longan* Fen Ke.

3. The method according to claim 1, wherein the alcohol is selected from the group consisting of methanol, ethanol, n-propanol, isopropanol, n-butanol, iso-butanol, sec-butanol, tert-butanol, and ethyl acetate or the solution thereof.

4. The method according to claim 1, wherein the alcohol extract of longan seeds comprises a fraction obtained by flash column chromatography; the column is 40 g Silica;
the flow rate is 18 mL/min; the mobile phase uses Solution A of ethyl acetate and Solution B of methanol; the gradient elution program is 100% Solution A and 0% Solution B at about 0 minute to about 30 minutes; 80% Solution A and 20% Solution B at about 31 minutes to about 45 minutes; 50% Solution A and 50% Solution B at about 46 minutes to about 65 minutes; 0% Solution A and 100% Solution B at about 66 minutes to about 85 minutes and at about 86 minutes to about 100 minutes.

5. The method according to claim 4, wherein the alcohol extract of longan seeds comprises a fraction obtained by flash column chromatography with the gradient elution program of 100% Solution A and 0% Solution B at about 0 minute to about 30 minutes.

6. The method according to claim 1, wherein the alcohol extract of longan seeds is prepared according to a process comprising:
(a) providing longan seeds;
(b) cutting the longan seeds into small pieces; and
(c) extracting the small pieces in step (b) with the alcohol to obtain an extract.

7. The method according to claim 6, wherein the temperature for the extracting in step (c) is about 30° C. to about 90° C.

8. The method according to claim 6, wherein the process further comprises a step (d) obtaining a liquid fraction from the extract.

9. The method according to claim 6, wherein step (c) further comprises:
(c1) extracting the small pieces in step (b) with an ethanol solution to obtain a rude extract;
(c2) lyophilizing the rude extract in step (c1); and (c3) extracting a product of lyophilizing in step (c2) with ethyl acetate to obtain an ethyl acetate fraction and a water fraction.

10. The method according to claim 9, wherein step (c) further comprises (c4) extracting the water fraction with n-butanol to obtain an n-butanol sub-fraction and a water sub-fraction.

11. The method according to claim 9, wherein the ethyl acetate fraction comprises a sub-fraction obtained by flash column chromatography; the column is 40 g Silica; the flow rate is 18 mL/min; the mobile phase uses Solution A of ethyl acetate and Solution B of methanol; the gradient elution program is 100% Solution A and 0% Solution B at about 0 minute to about 30 minutes; 80% Solution A and 20% Solution B at about 31 minutes to about 45 minutes; 50% Solution A and 50% Solution B at about 46 minutes to about 65 minutes; 0% Solution A and 100% Solution B at about 66 minutes to about 85 minutes and at about 86 minutes to about 100 minutes.

12. The method according claim 1, wherein the kidney tissue dysfunction is caused by renal tissue necrosis, hypertension, immune injury, diabetes mellitus, systemic lupus erythematosus, aging, long-term drug abuse, family inheritance, high-salt diet, obesity, high cholesterol, smoking, alcohol or nephrectomy.

13. The method according to claim 1, wherein the kidney tissue dysfunction is selected from the group consisting of excessively high blood and/or urine urinary protein, excessively high blood urea nitrogen, excessively high urine protein-creatinine ratio, excessively high blood and/or urine creatine kinase, excessively high blood and/or urine lactate dehydrogenase, excessively high blood and/or urine lactic acid and segmental sclerosis.

14. The method according to claim 1, wherein the kidney tissue dysfunction is nephritis.

* * * * *